US009797764B2

(12) United States Patent
Bluemner et al.

(10) Patent No.: US 9,797,764 B2
(45) Date of Patent: Oct. 24, 2017

(54) LIGHT ENHANCED FLOW TUBE

(71) Applicant: Spacelabs Healthcare LLC, Snoqualmie, WA (US)

(72) Inventors: Erik J. Bluemner, Verona, WI (US); George P. Kosmopoulos, Milton, WI (US)

(73) Assignee: Spacelabs Healthcare, LLC, Snoqualmie, WA (US)

( * ) Notice: Subject to any disclaimer, the term of this patent is extended or adjusted under 35 U.S.C. 154(b) by 89 days.

(21) Appl. No.: 14/312,566

(22) Filed: Jun. 23, 2014

(65) Prior Publication Data
US 2015/0107507 A1 Apr. 23, 2015

Related U.S. Application Data

(63) Continuation of application No. 12/775,719, filed on May 7, 2010, now Pat. No. 8,794,173.

(60) Provisional application No. 61/252,269, filed on Oct. 16, 2009.

(51) Int. Cl.
*G01F 23/64* (2006.01)
*G01F 1/22* (2006.01)
*A61M 16/01* (2006.01)

(52) U.S. Cl.
CPC ............ *G01F 23/64* (2013.01); *A61M 16/01* (2013.01); *G01F 1/22* (2013.01)

(58) Field of Classification Search
CPC ............ G01F 23/64; G01F 1/22; A61M 16/01
USPC ................ 116/200, 202, 227–228, 264, 266, 116/268–269, 271–274, 276, 304, DIG. 7, 116/DIG. 35; 73/273, 325, 326, 861.42, 73/861.52, 861.53, 861.55, 861.57, 861.3; 428/13
See application file for complete search history.

(56) References Cited

U.S. PATENT DOCUMENTS 2,808,580 A * 10/1957 Fuller ..................... G01F 1/24
250/230
2,820,651 A 1/1958 Phillips
2,912,858 A 11/1959 Fuller
2,944,547 A 7/1960 Ziherl
(Continued)

FOREIGN PATENT DOCUMENTS

CN 1688256 10/2005
CN 1781107 A 5/2006
(Continued)

OTHER PUBLICATIONS

International Search Report for PCT/US10/32635, Jul. 23, 2010.
(Continued)

Primary Examiner — R. A. Smith
Assistant Examiner — Tania Courson
(74) Attorney, Agent, or Firm — Novel IP

(57) ABSTRACT

An improved fluid flow gauging device includes a light enhanced acrylic block flow tube to optimize visualization of pressure readings. An LED or other light source is fitted to the top of the flow tube and illuminates a float or bobbin from above to provide more accurate readings, especially in low light conditions such as modern operating rooms. In addition, the light enhanced flow tube provides a mechanical backup in the case of failure of newer electronic systems and visually matches the graphical flow display, simultaneously providing a double-check of the electronic system.

12 Claims, 7 Drawing Sheets

(56) References Cited

U.S. PATENT DOCUMENTS

| | | | | |
|---|---|---|---|---|
| 3,517,639 | A | 6/1970 | Whitsel | |
| 3,608,545 | A | 9/1971 | Novack | |
| 3,618,592 | A | 11/1971 | Stewart | |
| 3,673,863 | A | 7/1972 | Spacek | |
| 3,689,908 | A * | 9/1972 | Ray | G01F 1/24 250/222.2 |
| 3,733,482 | A * | 5/1973 | Miller | F21S 6/002 362/216 |
| 3,757,577 | A * | 9/1973 | Bozek | G01P 13/0013 73/861.56 |
| 3,844,171 | A * | 10/1974 | Rodger | G01F 23/2927 385/12 |
| 3,897,606 | A | 8/1975 | Schleining | |
| 3,938,551 | A | 2/1976 | Henkin | |
| 3,954,010 | A * | 5/1976 | Hilblom | G01F 23/2933 73/291 |
| 3,981,329 | A | 9/1976 | Wohlwend | |
| 4,064,826 | A | 12/1977 | Pauli | |
| 4,148,312 | A | 4/1979 | Bird | |
| 4,167,115 | A | 9/1979 | Stoever | |
| 4,428,507 | A | 1/1984 | Sneider | |
| 4,513,294 | A | 4/1985 | Anderson | |
| 4,557,216 | A | 12/1985 | Demyon | |
| 4,625,731 | A | 12/1986 | Quedens | |
| 4,630,485 | A * | 12/1986 | Wastl, Sr. | G01F 1/22 73/861.56 |
| 4,630,486 | A | 12/1986 | Miles | |
| 4,643,693 | A * | 2/1987 | Rubinstein | A47G 33/00 40/406 |
| 4,697,450 | A | 10/1987 | Bachman | |
| 4,869,253 | A | 9/1989 | Craig, Jr. | |
| 4,879,997 | A | 11/1989 | Bickford | |
| 4,899,585 | A * | 2/1990 | Kulha | G01F 23/2925 340/619 |
| 4,903,222 | A | 2/1990 | Carter | |
| 4,944,305 | A | 7/1990 | Takatsu | |
| 4,991,576 | A | 2/1991 | Henkin | |
| 4,993,683 | A | 2/1991 | Kreuzer | |
| 5,087,906 | A | 2/1992 | Eaton | |
| 5,101,851 | A | 4/1992 | Abadi | |
| 5,144,898 | A | 9/1992 | Posly | |
| 5,197,480 | A | 3/1993 | Gebhardt | |
| 5,213,108 | A | 5/1993 | Bredesen | |
| 5,222,486 | A | 6/1993 | Vaughn | |
| 5,231,981 | A | 8/1993 | Schreiber | |
| 5,233,975 | A | 8/1993 | Choate | |
| 5,262,944 | A | 11/1993 | Weisner | |
| 5,291,182 | A | 3/1994 | Wiseman | |
| 5,292,564 | A * | 3/1994 | Lee | G09F 19/02 40/406 |
| 5,311,908 | A | 5/1994 | Barone | |
| 5,319,363 | A | 6/1994 | Welch | |
| 5,322,069 | A | 6/1994 | Gallant | |
| 5,331,549 | A | 7/1994 | Crawford, Jr. | |
| 5,333,106 | A | 7/1994 | Lanpher | |
| 5,339,826 | A | 8/1994 | Schmidt | |
| 5,348,008 | A | 9/1994 | Bornn | |
| 5,372,389 | A | 12/1994 | Tam | |
| 5,373,746 | A | 12/1994 | Bloss | |
| 5,419,332 | A | 5/1995 | Sabbah | |
| 5,438,983 | A | 8/1995 | Falcone | |
| 5,467,954 | A | 11/1995 | Wekell | |
| 5,473,536 | A | 12/1995 | Wimmer | |
| 5,482,050 | A | 1/1996 | Smokoff | |
| 5,497,766 | A | 3/1996 | Foster | |
| 5,502,853 | A | 4/1996 | Singleton | |
| 5,515,083 | A | 5/1996 | Casebolt | |
| 5,553,296 | A | 9/1996 | Forrest | |
| 5,558,418 | A | 9/1996 | Lambright | |
| 5,563,495 | A | 10/1996 | Tomiyori | |
| 5,584,291 | A | 12/1996 | Vapola | |
| 5,586,909 | A | 12/1996 | Saba | |
| 5,633,457 | A | 5/1997 | Kilar | |
| 5,682,526 | A | 10/1997 | Smokoff | |
| 5,684,504 | A | 11/1997 | Verhulst | |
| 5,687,717 | A | 11/1997 | Halpern | |
| 5,692,494 | A | 12/1997 | Pernetti | |
| 5,715,813 | A | 2/1998 | Guevrekian | |
| 5,718,235 | A | 2/1998 | Golosarsky | |
| 5,724,025 | A | 3/1998 | Tavori | |
| 5,724,985 | A | 3/1998 | Snell | |
| 5,749,367 | A | 5/1998 | Gamlyn | |
| 5,752,917 | A | 5/1998 | Fuchs | |
| 5,765,842 | A | 6/1998 | Phaneuf | |
| 5,779,305 | A | 7/1998 | Hocking | |
| 5,787,298 | A | 7/1998 | Broedner | |
| 5,800,360 | A | 9/1998 | Kisner | |
| 5,800,387 | A | 9/1998 | Duffy | |
| 5,819,741 | A | 10/1998 | Karlsson | |
| 5,855,550 | A | 1/1999 | Lai | |
| 5,868,133 | A | 2/1999 | DeVries | |
| 5,904,328 | A | 5/1999 | Leveridge | |
| 5,956,013 | A | 9/1999 | Raj | |
| 5,975,081 | A | 11/1999 | Hood | |
| 6,005,767 | A | 12/1999 | Ku | |
| 6,024,089 | A | 2/2000 | Wallace | |
| 6,042,548 | A | 3/2000 | Giuffre | |
| 6,048,044 | A | 4/2000 | Biggel | |
| 6,050,940 | A | 4/2000 | Braun | |
| 6,063,028 | A | 5/2000 | Luciano | |
| 6,096,025 | A | 8/2000 | Borders | |
| 6,099,093 | A | 8/2000 | Spence | |
| 6,131,571 | A | 10/2000 | Lampotang | |
| 6,134,537 | A | 10/2000 | Pao | |
| 6,146,523 | A | 11/2000 | Kenley | |
| 6,155,255 | A | 12/2000 | Lambert | |
| 6,188,407 | B1 | 2/2001 | Smith | |
| 6,269,813 | B1 | 8/2001 | Fitzgerald | |
| 6,322,502 | B1 | 11/2001 | Schoenberg | |
| 6,338,823 | B1 | 1/2002 | Furukawa | |
| 6,339,732 | B1 | 1/2002 | Phoon | |
| 6,347,310 | B1 | 2/2002 | Passera | |
| 6,349,436 | B1 | 2/2002 | Kreuzer | |
| 6,383,136 | B1 | 5/2002 | Jordan | |
| 6,396,583 | B1 | 5/2002 | Clare | |
| 6,424,860 | B1 | 7/2002 | Karlsson | |
| 6,435,690 | B1 | 8/2002 | Till | |
| 6,443,889 | B1 | 9/2002 | Groth | |
| D467,001 | S | 12/2002 | Buczek | |
| 6,488,029 | B1 | 12/2002 | Hood | |
| 6,536,430 | B1 | 3/2003 | Smith | |
| 6,541,758 | B2 * | 4/2003 | Yashiro | G01F 23/686 250/227.14 |
| 6,554,238 | B1 | 4/2003 | Hibberd | |
| 6,571,227 | B1 | 5/2003 | Agrafiotis | |
| 6,571,792 | B1 | 6/2003 | Hendrickson | |
| 6,591,694 | B2 | 7/2003 | Tsai | |
| 6,600,662 | B1 | 7/2003 | Emmert | |
| 6,647,341 | B1 | 11/2003 | Golub | |
| 6,650,779 | B2 | 11/2003 | Vachtesvanos | |
| 6,674,837 | B1 | 1/2004 | Taskar | |
| 6,692,258 | B1 | 2/2004 | Kurzweil | |
| 6,692,436 | B1 | 2/2004 | Bluth | |
| 6,699,187 | B2 | 3/2004 | Webb | |
| 6,702,754 | B2 | 3/2004 | Ogura | |
| 6,715,722 | B2 | 4/2004 | Roberts | |
| 6,735,648 | B2 | 5/2004 | Onishi | |
| 6,771,172 | B1 | 8/2004 | Robinson | |
| 6,796,264 | B1 * | 9/2004 | Appenzeller | G01F 1/056 116/112 |
| 6,804,656 | B1 | 10/2004 | Rosenfeld | |
| 6,824,539 | B2 | 11/2004 | Novak | |
| 6,829,501 | B2 | 12/2004 | Nielsen | |
| 6,931,795 | B1 | 8/2005 | Baloga | |
| 6,933,931 | B2 | 8/2005 | Lubarsky, Jr. | |
| 6,985,762 | B2 | 1/2006 | Brashears | |
| 7,006,865 | B1 | 2/2006 | Cohen | |
| 7,013,833 | B2 | 3/2006 | Lemberger | |
| 7,024,569 | B1 | 4/2006 | Wright | |
| 7,031,857 | B2 | 4/2006 | Tarassenko | |
| 7,038,588 | B2 | 5/2006 | Boone | |
| 7,040,175 | B1 * | 5/2006 | Huang | G01D 13/22 116/284 |

(56) References Cited

U.S. PATENT DOCUMENTS

| | | |
|---|---|---|
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,128,709 B2 | 10/2006 | Saruya |
| 7,137,951 B2 | 11/2006 | Pilarski |
| 7,193,233 B2 | 3/2007 | Smith |
| 7,216,802 B1 | 5/2007 | De La Huerga |
| 7,219,559 B2 * | 5/2007 | Sugi ............... G01F 1/24 73/861.56 |
| 7,223,007 B1 | 5/2007 | Fredley |
| 7,234,944 B2 | 6/2007 | Nordin |
| 7,256,708 B2 | 8/2007 | Rosenfeld |
| 7,265,676 B2 | 9/2007 | Gordon |
| 7,267,666 B1 | 9/2007 | Duchon |
| 7,282,029 B1 | 10/2007 | Poulsen |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |
| 7,386,340 B2 | 6/2008 | Schlegel |
| 7,468,032 B2 | 12/2008 | Stahmann |
| 7,469,601 B2 * | 12/2008 | Sugi ............... G01F 1/24 73/861.56 |
| 7,489,250 B2 | 2/2009 | Bock |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,540,187 B1 | 6/2009 | Dillon |
| 7,566,307 B2 | 7/2009 | Inukai |
| 7,621,500 B2 | 11/2009 | Ishizaki |
| 7,704,212 B2 * | 4/2010 | Wekell ............... A61B 5/0215 600/485 |
| 7,710,567 B1 * | 5/2010 | Mentzer ............ G01F 23/2924 250/577 |
| 7,751,878 B1 | 7/2010 | Merkle |
| 7,756,722 B2 | 7/2010 | Levine |
| 7,836,882 B1 | 11/2010 | Rumph |
| 7,945,452 B2 | 5/2011 | Fathallah |
| 7,974,924 B2 | 7/2011 | Holla |
| 8,002,701 B2 | 8/2011 | John |
| 8,027,846 B2 | 9/2011 | Schoenberg |
| 8,033,686 B2 | 10/2011 | Recker |
| 8,091,422 B2 * | 1/2012 | Felske ............... B63C 11/02 116/202 |
| 8,147,419 B2 | 4/2012 | Krauss |
| 8,190,900 B2 | 5/2012 | Corndorf |
| 8,233,272 B2 | 7/2012 | Fidacaro |
| 8,344,847 B2 | 1/2013 | Moberg |
| 8,398,408 B1 | 3/2013 | Hansen |
| 8,413,271 B2 | 4/2013 | Blanchard |
| 8,544,406 B2 * | 10/2013 | Fujihira ............... G01P 1/08 116/304 |
| 8,593,275 B2 | 11/2013 | Davis |
| 8,704,666 B2 | 4/2014 | Baker, Jr. |
| 8,798,527 B2 | 8/2014 | Gaines |
| 8,811,888 B2 | 8/2014 | Wiesner |
| 8,818,260 B2 | 8/2014 | Gaines |
| 8,855,550 B2 | 10/2014 | Gaines |
| 8,868,028 B1 | 10/2014 | Kaltsukis |
| 8,897,198 B2 | 11/2014 | Gaines |
| 8,903,308 B2 | 12/2014 | Wiesner |
| 8,922,330 B2 | 12/2014 | Moberg |
| 8,931,702 B2 | 1/2015 | Wekell |
| 8,940,147 B1 | 1/2015 | Bartsch |
| 8,943,168 B2 | 1/2015 | Wiesner |
| 9,020,419 B2 | 4/2015 | Gaines |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0026941 A1 | 3/2002 | Biondi |
| 2002/0032386 A1 | 3/2002 | Sackner |
| 2002/0060247 A1 | 5/2002 | Krishnaswamy |
| 2002/0108011 A1 | 8/2002 | Tanha |
| 2002/0161291 A1 | 10/2002 | Kianl |
| 2002/0173991 A1 | 11/2002 | Avitall |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | NecolaShehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0124866 A1 | 6/2005 | Elaz |
| 2005/0139213 A1 | 6/2005 | Blike |
| 2005/0146431 A1 | 7/2005 | Hastings |
| 2005/0148890 A1 | 7/2005 | Hastings |
| 2005/0151640 A1 | 7/2005 | Hastings |
| 2005/0177096 A1 | 8/2005 | Bollish |
| 2005/0229110 A1 | 10/2005 | Gegner |
| 2005/0251232 A1 | 11/2005 | Hartley |
| 2006/0004475 A1 | 1/2006 | Brackett |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0161295 A1 | 7/2006 | Yun |
| 2006/0199618 A1 | 9/2006 | Steer |

(56) References Cited

U.S. PATENT DOCUMENTS

| | | |
|---|---|---|
| 2006/0226992 A1 | 10/2006 | Al-Ali |
| 2006/0258926 A1 | 11/2006 | Ali |
| 2006/0280621 A1 | 12/2006 | Kinugawa |
| 2006/0282302 A1 | 12/2006 | Hussain |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0050715 A1 | 3/2007 | Behar |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | DePaepe |
| 2007/0176931 A1 | 8/2007 | Tivig |
| 2007/0180140 A1 | 8/2007 | Welch |
| 2007/0199388 A1 | 8/2007 | Furkert |
| 2007/0199566 A1 | 8/2007 | Be |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0077435 A1 | 3/2008 | Muradia |
| 2008/0103375 A1 | 5/2008 | Kiani |
| 2008/0117029 A1 | 5/2008 | Dohrmann |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0221418 A1 | 9/2008 | Al-Ali |
| 2008/0221495 A1 | 9/2008 | Steffens |
| 2008/0228045 A1 | 9/2008 | Gao |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0319331 A1 | 12/2008 | Zizzo |
| 2009/0005703 A1 | 1/2009 | Fasciano |
| 2009/0015116 A1 | 1/2009 | Arceta |
| 2009/0024008 A1 | 1/2009 | Brunner |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0099480 A1 | 4/2009 | Salgo |
| 2009/0117784 A1 | 5/2009 | Wu |
| 2009/0124239 A1 | 5/2009 | Tsuei |
| 2009/0131805 A1 | 5/2009 | OBrien |
| 2009/0133609 A1 | 5/2009 | Nethken |
| 2009/0149901 A1 | 6/2009 | Jayne |
| 2009/0151720 A1 | 6/2009 | Inoue |
| 2009/0182204 A1 | 7/2009 | Semler |
| 2009/0192541 A1 | 7/2009 | Ortiz |
| 2009/0193315 A1 | 7/2009 | Gower |
| 2009/0200902 A1 | 8/2009 | McKay |
| 2009/0206713 A1 | 8/2009 | Vilkas |
| 2009/0209849 A1 | 8/2009 | Rowe |
| 2009/0237264 A1 | 9/2009 | Bobey |
| 2009/0326340 A1 | 12/2009 | Wang |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1 | 6/2010 | Pierry |
| 2010/0156655 A1 | 6/2010 | Bullemer |
| 2010/0164452 A1 | 7/2010 | Ruan |
| 2010/0175695 A1 | 7/2010 | Jamison |
| 2010/0179400 A1 | 7/2010 | Brauker |
| 2010/0233891 A1 | 9/2010 | Broeksteeg |
| 2010/0238138 A1 | 9/2010 | Goertz |
| 2010/0259881 A1 | 10/2010 | Choi |
| 2010/0261979 A1 | 10/2010 | Kiani |
| 2010/0285771 A1 | 11/2010 | Peabody |
| 2010/0294405 A1 | 11/2010 | Longinotti-Buitoni |
| 2010/0298656 A1 | 11/2010 | McCombie |
| 2010/0298718 A1 | 11/2010 | Gilham |
| 2010/0318578 A1 | 12/2010 | Treu |
| 2010/0324380 A1 | 12/2010 | Perkins |
| 2010/0324384 A1 | 12/2010 | Moon |
| 2010/0324936 A1 | 12/2010 | Vishnubhatla |
| 2011/0004071 A1 | 1/2011 | Faiola |
| 2011/0071420 A1 | 3/2011 | Pierre |
| 2011/0077971 A1 | 3/2011 | Surwit |
| 2011/0087756 A1 | 4/2011 | Biondi |
| 2011/0088694 A1 | 4/2011 | Tobia |
| 2011/0125040 A1 | 5/2011 | Crawford |
| 2011/0130798 A1 | 6/2011 | Elghazzawi |
| 2011/0138323 A1 | 6/2011 | Skidmore |
| 2011/0152629 A1 | 6/2011 | Eaton |
| 2011/0164074 A1 | 7/2011 | Frank |
| 2011/0190643 A1 | 8/2011 | Zhang |
| 2011/0225771 A1 | 9/2011 | Bartnick |
| 2011/0245579 A1 | 10/2011 | Bruggeman |
| 2011/0257489 A1 | 10/2011 | Banet |
| 2011/0279383 A1 | 11/2011 | Wilson |
| 2011/0279958 A1 | 11/2011 | Clark |
| 2012/0030610 A1 | 2/2012 | DiPerna |
| 2012/0041786 A1 | 2/2012 | Yu |
| 2012/0075327 A1 | 3/2012 | Mackenzie |
| 2012/0095778 A1 | 4/2012 | Gross |
| 2012/0105233 A1 | 5/2012 | Bobey |
| 2012/0105774 A1 | 5/2012 | Fletcher |
| 2012/0127103 A1 | 5/2012 | Qualey |
| 2012/0209984 A1 | 8/2012 | Gonzalez-Banos |
| 2012/0232398 A1 | 9/2012 | Roham |
| 2012/0330675 A1 | 12/2012 | Muradia |
| 2013/0015966 A1 | 1/2013 | Soomro |
| 2013/0162426 A1 | 6/2013 | Wiesner |
| 2013/0267861 A1 | 10/2013 | Vassallo |
| 2014/0153747 A1 | 6/2014 | Contolini |

FOREIGN PATENT DOCUMENTS

| | | |
|---|---|---|
| CN | 1943505 A | 4/2007 |
| CN | 1983258 A | 6/2007 |
| CN | 101194278 | 6/2008 |
| DE | 9415672 | 11/1994 |
| DE | 102006011151 | 9/2007 |
| EP | 0686900 A2 | 12/1995 |
| EP | 0955007 A1 | 11/1999 |
| EP | 1054338 | 11/2000 |
| EP | 1227752 A1 | 5/2001 |
| EP | 1449558 | 8/2004 |
| EP | 1852060 | 11/2007 |
| EP | 1868123 A1 | 12/2007 |
| EP | 2555668 A2 | 2/2013 |
| EP | 2805564 A4 | 9/2015 |
| GB | 191214095 | 0/1912 |
| GB | 568212 | 3/1945 |
| GB | 2389290 A | 12/2003 |
| JP | 07163527 | 6/1995 |
| JP | 2003210422 | 7/2003 |
| WO | 9415523 | 7/1994 |
| WO | 9918705 | 4/1999 |
| WO | 03091841 | 11/2003 |
| WO | 03102850 | 12/2003 |

(56) References Cited

FOREIGN PATENT DOCUMENTS

| | | |
|---|---|---|
| WO | 2004038669 A1 | 5/2004 |
| WO | 2005101276 A3 | 10/2005 |
| WO | 2005114524 A3 | 12/2005 |
| WO | 2006094055 A2 | 9/2006 |
| WO | 2010126916 | 11/2010 |
| WO | 2010126916 A1 | 11/2010 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |
| WO | 2014055660 A1 | 4/2014 |
| WO | 2014194193 | 12/2014 |

OTHER PUBLICATIONS

Office Action dated Aug. 14, 2014 for U.S. Appl. No. 12/768,714.
Office Action dated Feb. 26, 2015 for U.S. Appl. No. 12/768,714.
Office Action dated Jan. 17, 2013 for U.S. Appl. No. 12/768,714.
Office Action dated Jun. 18, 2012 for U.S. Appl. No. 12/768,714.
Office Action dated Nov. 21, 2013 for U.S. Appl. No. 12/768,714.
Office Action dated Oct. 7, 2015 for U.S. Appl. No. 12/768,714.
Chinese Office Action, Patent Application No. 201180025170X, Issued Apr. 21, 2014, First OA.
Second Office Action, Chinese Patent Application No. 201180025170X, Issued Jun. 7, 2015.
Third Office Action, Chinese Patent Application No. 201180025170X, dated Dec. 10, 2015.
Office Action dated Oct. 2, 2015 for U.S. Appl. No. 14/044,524.
First Office Action, Chinese Patent Application No. 201180067543.X, Jun. 2014.
Second Office Action for Chinese Patent Application No. 201180067543.X, dated Nov. 11, 2015.
Office Action dated Feb. 11, 2016 for U.S. Appl. No. 13/895,281.
International Preliminary Report on Patentability for PCT/US2011/061554, Feb. 25, 2014.
International Search Report for PCT/US2011/061554, Feb. 14, 2014.
International Search Report for PCT/US2011/061555, Apr. 17, 2012.
International Search Report for PCT/US2011/061558, Aug. 10, 2012.
International Search Report for PCT/US2011/61557, Apr. 23, 2012.
Office Action dated Jul. 2, 2015 for U.S. Appl. No. 13/895,527.
Office Action dated Feb. 10, 2016 for U.S. Appl. No. 13/895,270.
International Preliminary Report on Patentability, PCT/US2011/028007, Sep. 17, 2013, International Search Authority.
International Search Report, PCT/US2011/028007, Jul. 11, 2011, International Search Authority.
Office Action dated Aug. 6, 2015 for U.S. Appl. No. 13/045,539.
Office Action dated Nov. 21, 2014 for U.S. Appl. No. 13/045,539.
Office Action dated Feb. 9, 2016 for U.S. Appl. No. 13/045,539.
European Search Report for EP12786443.7, Apr. 15, 2015.
First Office Action, Chinese Patent Application No. 2012800351488, Jun. 13, 2015.
IntelliVue Patient Monitor; MP20/30, MP40/50, MP60/70/80/90, Release G.0 with Software Revision G.Ox.xx (Philips) Sep. 2008; pp. 4, 10, 19, 20, 46-49, 82, 326, 348, 420, 422, 424, 452; Accessed on Sep. 30, 2013; <http://www.mc.vanderbilt.edu/documents/nursingeducationresources/files/MP20-MP90%20Instructions%20for%20Use%20Manual%20Rev_G_0%20%20English%20M8000-9001k.pdf>.
International Preliminary Report on Patentability, PCT/US12/38000, Nov. 13, 2013.
International Preliminary Report on Patentability, PCT/US2006/007269, Sep. 11, 2007, Spacelabs Medical.
International Preliminary Report on Patentability, PCT/US2011/065678, Jun. 18, 2013, International Search Authority.
International Preliminary Report on Patentability, PCT/US2011/065685, Jun. 18, 2013.
International Search Report, PCT/US2011/065685, May 08, 2012, International Search Authority.
International Search Report for PCT/US06/07269, Aug. 28, 2006.
International Search Report for PCT/US10/34025, Aug. 9, 2010.
International Search Report for PCT/US12/38000, Oct. 23, 2012.
International Search Report for PCT/US2010/052977, Mar. 18, 2011.
International Search Report for PCT/US2011/029278, Aug. 2, 2011.
International Search Report for PCT/US2011/065676, Sep. 20, 2012.
International Search Report for PCT/US2011/065678, Jun. 29, 2012.
International Search Report for PCT/US2012/060125, Apr. 19, 2013.
International Search Report for PCT/US2013/063087, Mar. 6, 2014.
International Search Report for PCT/US2014/040225, Nov. 5, 2014.
Notice of Allowance dated Jan. 28, 2015 for U.S. Appl. No. 13/300,478.
Notice of Allowance dated Jan. 8, 2015 for U.S. Appl. No. 13/329,259.
Notice of Allowance dated Mar. 13, 2015 for U.S. Appl. No. 12/906,081.
Notice of Allowance dated May 11, 2015 for U.S. Appl. No. 13/300,462.
Notice of Allowance dated May 27, 2015 for U.S. Appl. No. 14/165,193.
Notice of Allowance dated Oct. 31, 2014 for U.S. Appl. No. 12/114,689.
Notice of Allowance dated Sep. 3, 2014 for U.S. Appl. No. 13/973,862.
Office Action dated Apr. 16, 2015 for U.S. Appl. No. 14/557,135.
Office Action dated Apr. 24, 2015 for U.S. Appl. No. 13/651,337.
Office Action dated Apr. 7, 2015 for U.S. Appl. No. 13/472,332.
Office Action dated Aug. 1, 2011 for U.S. Appl. No. 11/716,513.
Office Action dated Aug. 28, 2009 for U.S. Appl. No. 11/716,513.
Office Action dated Aug. 4, 2015 for U.S. Appl. No. 13/329,219.
Office Action dated Dec. 10, 2014 for U.S. Appl. No. 14/165,193.
Office Action dated Jul. 2, 2012 for U.S. Appl. No. 11/716,513.
Office Action dated Jun. 18, 2015 for U.S. Appl. No. 13/329,186.
Office Action dated Mar. 23, 2010 for U.S. Appl. No. 11/716,513.
Office Action dated May 21, 2015 for U.S. Appl. No. 13/300,526.
Office Action Dated May 31, 2013 for U.S. Appl. No. 13/052,883.
Office Action dated Nov. 12, 2014 for U.S. Appl. No. 13/300,462.
Office Action dated Sep. 22, 2014 for U.S. Appl. No. 13/329,186.
Partial European Search Report for EP 12839321.2, May 26, 2015.
Schoenberg, Roy, MD; Sands, Daniel Z., Md Mph; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
Supplemental Notice of Allowance dated Apr. 20, 2015 for U.S. Appl. No. 12/906,081.
Supplementary European Search Report, Nov. 25, 2009, Spacelabs Medical, PCT/ US2006/007269.
Office Action dated Jan. 20, 2016 for U.S. Appl. No. 13/651,337.
Office Action mailed Jan. 6, 2016 for U.S. Appl. No. 13/329,219.
Office Action dated Oct. 14, 2015 for U.S. Appl. No. 14/460,147.
Office Action for Chinese Patent Application No. 201080057413.3, Oct. 10, 2015.
Office Action for Chinese Patent Application No. 2011800707731, Sep. 29, 2015.

(56) References Cited

OTHER PUBLICATIONS

Office Action for Chinese Patent Application No. 2011800655173, May 15, 2015.
Extended European Search Report, EP 11861868.5, Sep. 28, 2015.
International Search Report for PCT/US2013/041246, Dec. 9, 2013.
International Search Report for PCT/US2013/041247, Jan. 10, 2014.
Notice of Allowance dated Nov. 18, 2015 for U.S. Appl. No. 14/557,135.
Office Action dated Nov. 13, 2015 for U.S. Appl. No. 13/472,332.
"BleaseSirius Anesthesia Systems User Manual 1073-0212-00/Rev. B", Dec. 1, 2010, pp. 1-258, XP055209666.
"Lifegard II Patient Monitor Operators Manual", Jan. 1, 2006, pp. 1-1, XP055209485.
Extended European Search Report for EP12839321, Dec. 1, 2015.

\* cited by examiner

LIGHT ENHANCED FLOW TUBE

CROSS REFERENCE OF THE INVENTION

The present invention relies on U.S. Provisional Application No. 61/252,269, filed on Oct. 16, 2009, for priority, and incorporates the specification and drawings of this application by reference in its entirety.

FIELD OF THE INVENTION

The present invention relates to gas and liquid flow gauging devices. More particularly, the present invention relates to a light enhanced flow tube with a bobbin used as a measure of flow in anesthesia systems.

BACKGROUND OF THE INVENTION

Historically, transparent tubes containing a float or "bobbin" have been used as a means of measuring flow in gas and liquid systems. Visually observing the level of the bobbin alongside scaled markings on a plastic strip adjacent to the tube or printed on the walls of the tube itself, enables users to accurately gauge the flow of gas or liquid being applied to the system. Traditionally, such gauging devices have utilized an elongated illumination source positioned behind the flow tube and scale strip. While providing an extremely reliable means for measuring flow, this traditional method is difficult to read accurately and does not provide for optimal visualization when used in low light conditions, such as those found in today's operating rooms.

Lengthwise illumination of the flow tube along with illumination of a needle gauge has been used to assist the user in taking readings. For example, United States Patent Application Number 20080251003, assigned to Aviation Oxygen Systems, Inc., describes "[a]n illuminated gas flow tube comprises an in-line flow tube having a distal end and a proximal end. A gas inlet is co-axially secured to the distal end, and a gas outlet is co-axially secured to the proximal end. A specific gravity ball is located within the in-line flow tube, and moves within the flow tube as a function of gas entering the gas inlet. A phosphorescent or photoluminescent material is configured and arranged to at least partially lengthwise surround a radial exterior portion of the flow tube to illuminate the interior of the tube. An illuminated gas pressure gauge comprises an gas inlet, a pressure sensing element, a transparent cover, and a face that is encased by and seen through the transparent cover, where the face includes markings indicative of pressure. A needle is operatively connected to the pressure sensing element and seen through the transparent cover to provide a visual indication of pressure at the gas inlet, where the face is coated with an illuminating material that allows the gauge to be read in low light conditions."

In addition, newer flow gauging devices, specifically those used in modern anesthesia machines, now use electronic flow measurement and display the data graphically on a video user interface. These newer systems have the advantage of providing digital outputs and enabling the user to directly input the flow data into the patient's records.

Although these new electronic devices provide accurate and visually appealing flow data, a need exists to provide a reliable flow tube device that works via a mechanical method in the event of electronic system failure. The user will also desire the mechanical flow tube as a "double check" of the digital data. In addition, the mechanical flow tube device needs to display the flow data in a manner that matches newer electronic displays and can be read optimally in low light conditions.

SUMMARY OF THE INVENTION

In one embodiment, the present invention is a light enhanced flow tube with a bobbin used as a measure of flow in anesthesia systems.

In one embodiment, the present invention is a fluid flow gauging device comprising a container encasing a hollow tube having a length, a bottom and a top, wherein an inlet port is positioned proximate to the bottom of the hollow tube, wherein an opening is positioned proximate to the top of the hollow tube, and wherein an outlet port is positioned proximate to the top of the hollow tube; a bobbin located within the hollow tube, said bobbin capable of traversing the length of the hollow tube dependent upon the amount of fluid pressure applied; and a fiber optic pipe used to direct light from a light source through the top of said hollow tube and toward said bobbin.

In one embodiment, the bobbin is spherical and has a reflective quality. In one embodiment, the bobbin is a white alumina ceramic ball. In another embodiment, the bobbin is a stainless steel ball.

In one embodiment, said container comprises at least one unitary piece of acrylic, wherein said unitary piece of acrylic is an acrylic block. Additionally, said container comprises at least one beveled face having a plurality of scale markings proximate to said at least one beveled face.

In one embodiment, the fiber optic pipe is fixedly attached to said opening positioned proximate to the top of the hollow tube. In one embodiment, the light source comprises a remotely located LED, wherein said LED is powered by an energy source independent of an energy source that causes a flow of fluid through said hollow tube.

In one embodiment, the inlet port is configured to receive pressurized gas into said hollow tube and the outlet port is configured to enable an exit of said pressurized gas from said hollow tube. In one embodiment, the tube is cylindrical.

In one embodiment, a mechanism automatically switches on said light source when fluid flows. In one embodiment, said mechanism comprises a pressure transducer measuring the pressure rise through the resistance of the flow meter. In another embodiment, said mechanism comprises a switch on the flow control needle valve. In one embodiment, when fluid is caused to flow through said hollow tube, said fiber optic pipe illuminates a top hemisphere of said bobbin.

In another embodiment, the present invention is a fluid flow gauging device comprising a container encasing a hollow tube having a length, a bottom and a top, wherein an inlet port is positioned proximate to the bottom of the hollow tube, wherein an opening is positioned proximate to the top of the hollow tube, and wherein an outlet port is positioned proximate to the top of the hollow tube; a bobbin located within the hollow tube, said bobbin capable of traversing the length of the hollow tube dependent upon the amount of fluid pressure applied; and a light emitting diode (LED) used to project light through the top of said hollow tube and toward said bobbin.

In yet another embodiment, the present invention is a fluid flow gauging device comprising a container encasing a hollow tube having a length, a bottom and a top, wherein an inlet port is positioned proximate to the bottom of the hollow tube, wherein an opening is positioned proximate to the top of the hollow tube, and wherein an outlet port is positioned proximate to the top of the hollow tube; a bobbin located within the hollow tube, said bobbin capable of traversing the length of the hollow tube dependent upon the amount of fluid pressure applied; and a light source directed through the top of said hollow tube and toward said bobbin.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1:
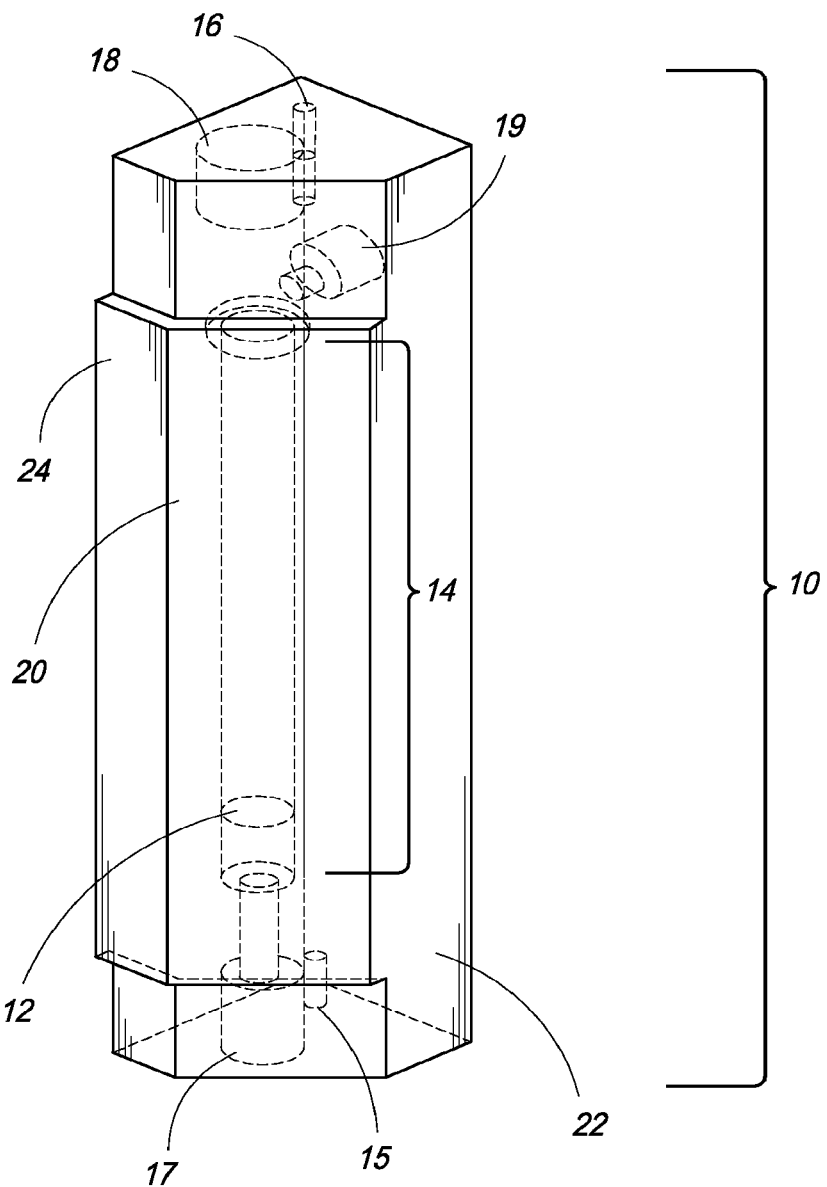
FIG. 1 is a three-dimensional diagram illustrating a number of the components of the light enhanced flow tube of the present invention.

In one embodiment, the present invention is directed towards an improved fluid flow, such as any gas or liquid, gauging device in the form of a light enhanced flow tube.

In one embodiment, the present invention is directed towards a flow tube encased in an acrylic block, said flow tube containing a float or "bobbin", said bobbin being illuminated from the top in an effort to enhance visualization of the bobbin, thereby enabling the user to make more accurate flow readings. The illumination is supplied via a light emitting diode (LED) or other light source and shines down from the top of the tube onto the bobbin. In one embodiment, the bobbin is spherical and of a reflective material so as to enhance visualization when illuminated from above. The prismatic effect of the acrylic block flow tube combined with the illumination of the bobbin allow for clearer visualization of the bobbin level and therefore more accurate flow readings, especially in low light conditions. The combined effects also allow the user to make accurate flow readings at more extreme viewing angles relative to front face of a traditional flow tube.

Further, the present invention is directed towards the use of a spherical, white alumina ceramic indicator ball as the bobbin. This particular type of bobbin reflects blue light from an LED driven light pipe in a visually appealing manner. The white alumina ceramic indicator ball does so by "spreading" light around its surface, illuminating the whole upper hemisphere. This type of bobbin enhances visualization more effectively than a stainless steel ball, which reflects light more as a point. In addition, since the reflected light spreads over the entire upper hemisphere, it forms a natural light to dark line at the center of the ball, exactly where the user should take the visual flow reading.

Still further, the angled face flow tube design allows for optimal viewing when the light enhanced flow tube is mounted on an anesthesia machine adjacent to the electronic flow tube screen. This invention provides an updated implementation of older flow tube technology, offering the user better visualization of the bobbin while simultaneously providing a better visual convergence of newer electronic flow measurement displays and older flow tube technology used as a backup measurement source. The angled face flow tube design allows for the floating illuminated sphere to be viewed from directly in front of the electronic flow tube screen even though the bezel for the front display is physically in between the bobbin and the user's eyes. The bend of light at the angled face allows this visualization to occur and keeps the area consumed by the front face of the flow tube small.

Still further, the light used to illuminate the bobbin is supplied via a fiber optic light pipe that is introduced into a sealed fitting at the top of the flow tube. This allows the source LED to be mounted on a circuit board some distance removed from the flow tube, enabling more economical and practical packaging.

Still further, the illumination would only be turned on when flow is being applied to the system. This could be effectuated with a separate electronic mechanism. This will result in the added benefit of information projection lighting. If the flow is turned on, the bobbin will automatically illuminate, resulting in enhancing the bobbin reading because of the light. In addition, operating rooms and other areas of hospitals often have auxiliary oxygen flow tubes that will waste $O_2$ gas if mechanically left on. By having the illumination turned on only when flow is applied, the user will be able to observe if the bobbin is illuminated and know that the flow has been inadvertently left on.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is a three dimensional diagram illustrating a number of the components of the light enhanced flow tube 14. In one embodiment, the light enhanced flow tube 14 is contained within an acrylic block 10. Further, flow tube 14 comprises an inlet port 17 positioned at the bottom of the acrylic block 10, an outlet port 19 exiting to the back of the acrylic block 10, an opening 18 for a sealed fitting for a fiber optic light pipe, and a bobbin 12 located within flow tube 14. The bobbin 12 can be any structure capable of floating in a fluid flow, including a float, a bob, a buoyant particle, or any other such structure. In one embodiment, the acrylic block 10 has a mounting hole 16 positioned at the top and a mounting hole 15 positioned at the bottom. In one embodiment, the acrylic block 10 has five sides, comprising a left side, a back side, a non-beveled portion of the right side 22, a beveled right side 20, and a beveled front face 24 to optimize visualization of bobbin 12.

Figure 2A:
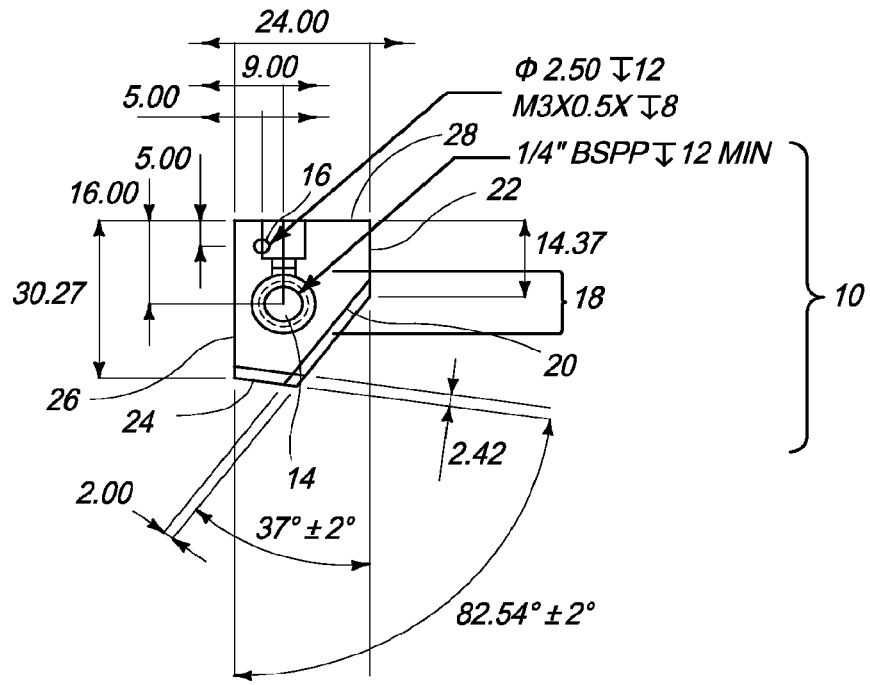
FIG. 2A is an illustration of the top view of the light enhanced flow tube, depicting the opening for a light pipe and various measurements included in one embodiment of the present invention.

In one embodiment, the acrylic block 10 has a beveled front face 24 and a partially beveled right side 20 to enhance visualization of the bobbin 12 from multiple and extreme viewing angles. FIG. 2A is an illustration of the top view of the light enhanced flow tube 14, depicting the opening for a light pipe 18 and various measurements included in one embodiment of the present invention. In one embodiment, the back side 28 of acrylic block 10 measures 24.00 millimeters across and forms a 90 degree angle with the left side 26 when facing the front face 24 of the acrylic block 10. In one embodiment, the left side 26 measures 30.27 millimeters. In an additional embodiment, the left side 26 and back side 28 of the flow tube are covered with an opaque label or ink of contrasting color to further enhance the visual effect of the bobbin's illumination. In one embodiment, this color is a light grey. In one embodiment, the non-beveled portion of the right side 22 when facing the front face 24 forms a 90 degree angle with the back side 28 of the acrylic block 10 and measures 14.37 millimeters. In one embodiment, the beveled portion of the right side 20 forms a 37+/−2 degree angle with the non-beveled portion of the right side 22 and extends inward toward the left side 26 of the acrylic block 10. In one embodiment, the beveled front face 24 forms an 82.54+/−2 degree angle with the left side 26 and extends outward away from the center of the acrylic block 10.

As shown in FIG. 2A, in one embodiment, the center of the flow tube 14 is positioned 9.00 millimeters in from the left side 26 when facing the front face 24 and 16.00 millimeters in from the back of the acrylic block 10. In one embodiment, the flow tube 14 extends substantially from the bottom of the acrylic block 10 to substantially to the top of the acrylic block 10, where an opening for a sealed fitting 18 for a fiber optic light pipe is located. In one embodiment, the opening 18 for the light pipe is ¼ inch diameter British Standard Pipe Parallel thread (BSPP) and extends vertically at least 12.00 millimeters down into the acrylic block 10. In one embodiment, the center of the opening 18 for the light pipe at the top of the acrylic block 10 is positioned 9.00 millimeters in from the left side 26 when facing the front face 24 and 16.00 millimeters in from the back side 28 of the acrylic block 10, in line with the center of the flow tube 14. The flow tube 14 is wider at the top and narrower at the bottom, with its cross section varying as a function of calibration gas and the weight of the bobbin 12. The bobbin 12 traverses the length of the flow tube 14 up to the light pipe lens at the top and down to the narrower portion at the bottom. The lens at the top of the flow tube 14 prevents further travel of the bobbin 12 up the flow tube 14 and the smaller diameter at the bottom of the flow tube 14 prevents further travel of the bobbin 12 down the flow tube 14. The bobbin 12 traverses up and down the flow tube 14 dependent upon the amount of flow passing through the flow tube 14. In one embodiment, a mounting hole 16 is positioned at the top of the acrylic block 10. In one embodiment, the mounting hole 16 at the top of the acrylic block 10 is 2.50 millimeters in diameter and extends vertically at least 12.00 millimeters down into the acrylic block 10. In one embodiment, the center of the mounting hole 16 at the top of the acrylic block 10 is positioned 5.00 millimeters in from the left side 26 when facing the front face 24 and 5.00 millimeters in from the back side 28 of the acrylic block 10.

Figure 2B:
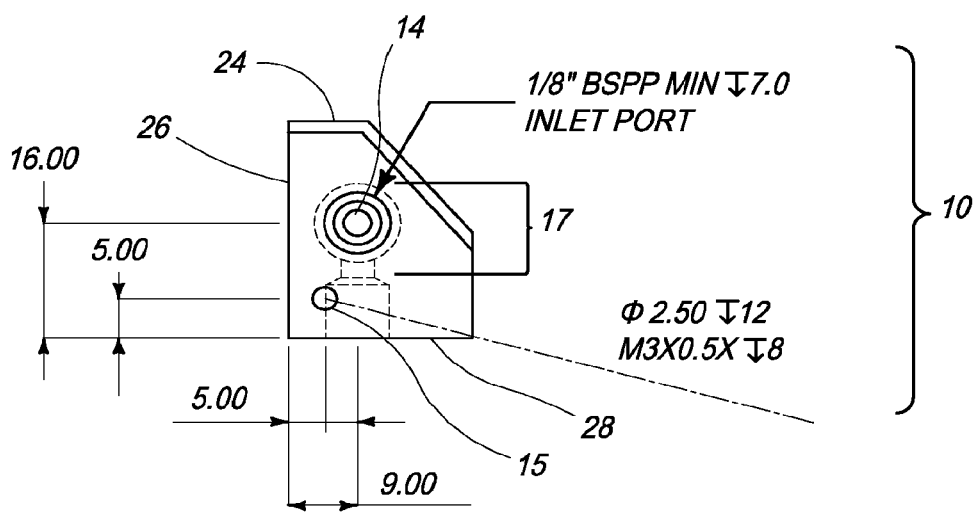
FIG. 2B is an illustration of the bottom view of the light enhanced flow tube, depicting an inlet port and various measurements included in one embodiment of the present invention.

FIG. 2B is an illustration of the bottom view of the light enhanced flow tube 14, depicting the inlet port 17 and various measurements included in one embodiment of the present invention. The inlet port 17 is located at the bottom of the acrylic block 10 and serves to receive pressurized gas into the flow tube 14. As shown in FIG. 2B, in one embodiment, the inlet port 17 positioned at the bottom of the acrylic block 10 is ⅛ inch diameter BSPP and extends vertically at least 7.00 millimeters up into the acrylic block 10. In one embodiment, the center of the inlet port 17 is positioned 9.00 millimeters in from the left side 26 when facing the front face 24 and 16.00 millimeters in from the back side 28 of the acrylic block 10, in line with the center of the flow tube 14. In one embodiment, a mounting hole 15 is positioned at the bottom of the acrylic block 10. In one embodiment, the mounting hole 15 at the bottom of the acrylic block 10 is 2.50 millimeters in diameter and extends vertically at least 12.00 millimeters up into the acrylic block 10. In one embodiment, the center of the mounting hole 15 at the bottom of the acrylic block 10 is positioned 5.00 millimeters in from the left side 26 when facing the front face 24 and 5.00 millimeters in from the back side 28 of the acrylic block 10.

Figure 2C:
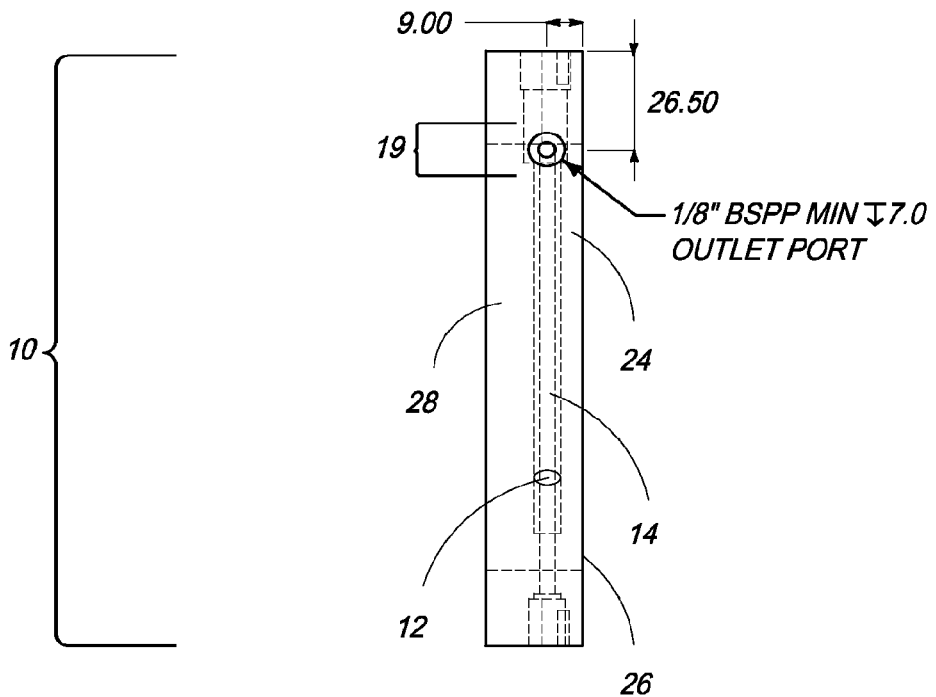
FIG. 2C is an illustration of the back view of the light enhanced flow tube, depicting an outlet port and various measurements included in one embodiment of the present invention.

FIG. 2C is an illustration of the back view of the light enhanced flow tube 14, depicting the outlet port 19 and various measurements included in one embodiment of the present invention. The outlet port 19 is located on the back of the acrylic block 10 and serves as a point for the pressurized gas to exit the flow tube 14. As shown in FIG. 2C, in one embodiment, the outlet port 19 exiting to the back of the acrylic block 10 is ⅛ inch diameter BSPP and extends horizontally at least 7.00 millimeters into the acrylic block 10 at which point it connects with the flow tube 14. In one embodiment, the center of the outlet port 19 is positioned 9.00 millimeters in from the left side 26 when facing the front face 24 and 26.50 millimeters down from the top of the acrylic block 10.

Figure 2D:
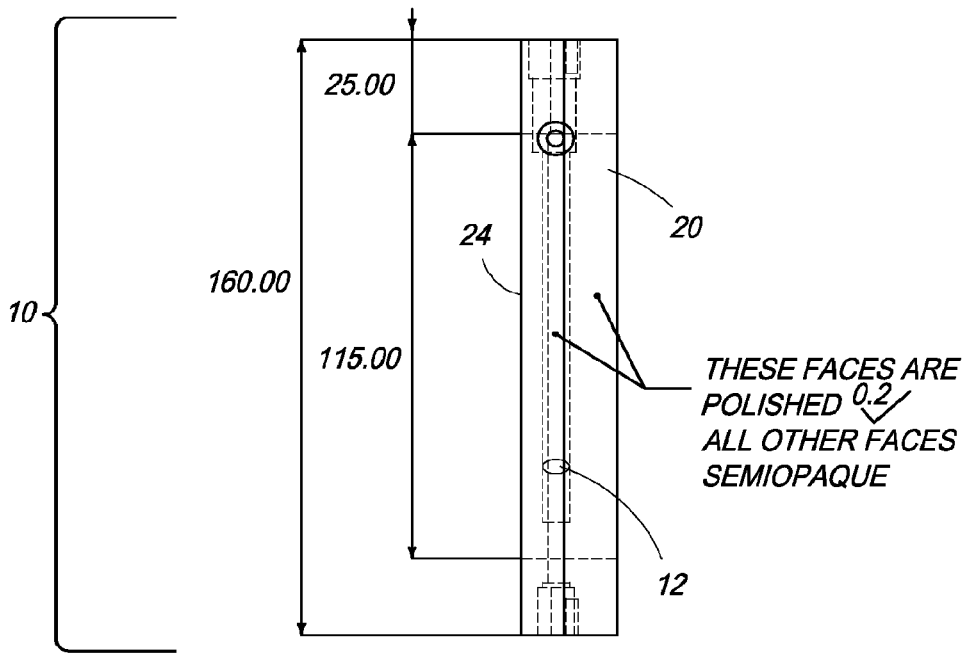
FIG. 2D is an illustration of the front face view of the light enhanced flow tube, depicting the beveled front face, beveled right side, and various measurements included in one embodiment of the present invention.

FIG. 2D is an illustration of the front face view of the light enhanced flow tube 14, depicting the beveled front face 24, beveled right side 20, and various measurements included in one embodiment of the present invention. As shown in FIG. 2D, in one embodiment, the total length of the acrylic block 10 measures 160.00 millimeters. With reference to FIGS. 2A and 2D simultaneously, in one embodiment, for the first 25 millimeters from the top of the acrylic block 10, the beveled portion of the right side 20 recedes 2.00 millimeters back toward the center of the acrylic block 10. After the first 25.00 millimeters, the beveled right side 20 extends back outward 2.00 millimeters and continues at this measurement for another 115.00 millimeters. At this point, the beveled right side 20 again recedes 2.00 millimeters back towards the center of the acrylic block 10 and continues in this manner another 20.00 millimeters to the bottom of the acrylic block 10. Further, in one embodiment, for the first 25 millimeters from the top of the acrylic block 10, the beveled front face 24 recedes 2.42 millimeters back toward the center of the acrylic block 10. After the first 25.00 millimeters, the beveled front face 24 extends back outward 2.42 millimeters and continues at this measurement for another 115.00 millimeters. At this point, the beveled front face again recedes 2.42 millimeters back towards the center of the acrylic block 10 and continues in this manner another 20.00 millimeters to the bottom of the acrylic block 10.

In one embodiment, the fully extended beveled front face and fully extended beveled portion of the right side are polished and all the remaining surfaces are semi-opaque or fully opaque and contain a contrasting color. The polished surfaces and bending of light at these beveled faces allows optimal visualization while simultaneously keeping the area consumed by the front face of the light enhanced acrylic block flow tube relatively small when positioned adjacent to the electronic graphical display.

In one embodiment, the light enhanced acrylic block flow tube is calibrated for $O_2$ gas and is chemically compatible with $O_2$, $N_2O$, and air. In one embodiment, the pressure range is 0-14 kPa GA and the flow range is 0-15 LPM.

Figure 3:
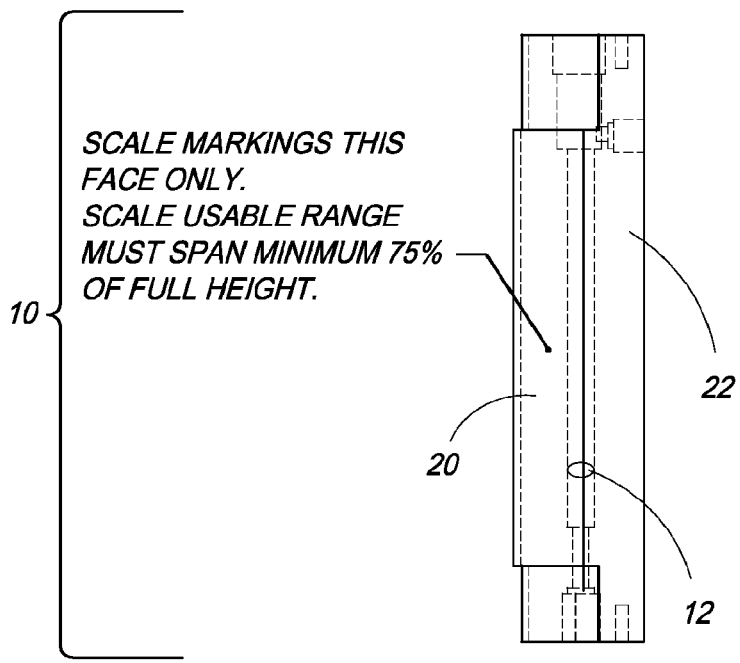
FIG. 3 is an illustration of the right side profile view of the light enhanced flow tube.

FIG. 3 is an illustration of the right side profile view of the light enhanced flow tube 14. In one embodiment, the beveled right side 20 contains white scale markings at 0, 5, 10, and 15 LPM, with ticks every 1 LPM. The scale markings include a 'Read at Center' symbol and a 'L/Min' label. In one embodiment, only the fully extended beveled right side 20 contains markings and the scale usable range spans a minimum of 75% of the full height of said fully extended beveled right side 20.

Figure 4:
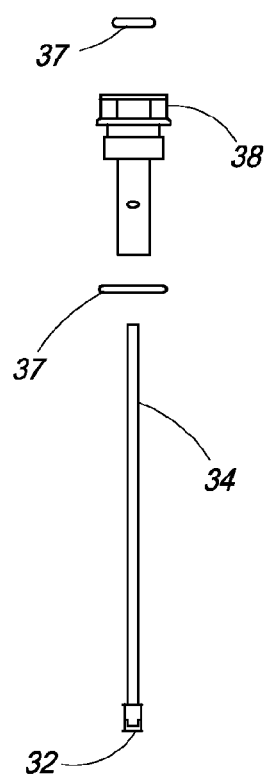
FIG. 4 is a diagram separately illustrating a number of the components of the fiber optic light pipe assembly.
Figure 5:
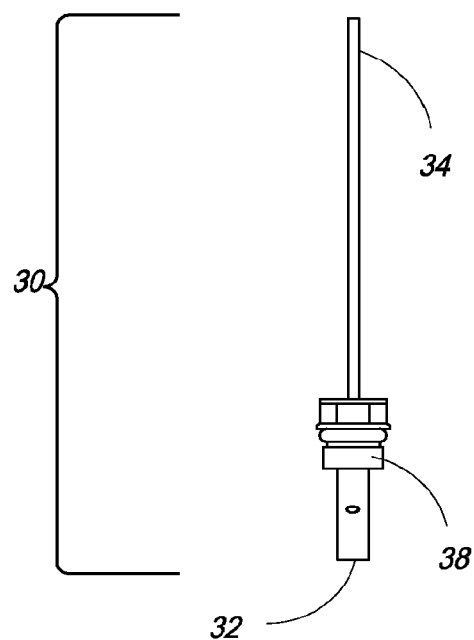
FIG. 5 is a diagram illustrating a fully assembled fiber optic light pipe assembly.

FIG. 4 is a diagram separately illustrating a number of the components of the fiber optic light pipe assembly 30, as shown assembled in FIG. 5. In one embodiment, the fiber optic light pipe assembly includes a fiber optic pipe 34 that terminates with a lens 32 on one end and connects to an LED on the other end. This allows the source LED to be mounted on a circuit board remote from the flow tube, enabling more economical and practical packaging. In one embodiment, the fiber optic pipe 34 is encircled by a plug top 38 that has a thread fitting that matches the top opening of the acrylic block. In one embodiment, an o-ring or washer 36 is positioned between the plug top 38 and the opening at the top of the acrylic block. A smaller o-ring or washer 37 is positioned above the plug top 38. In one embodiment, a silicone based adhesive sealant is applied to completely cover the o-ring or washer 37 and around the fiber optic pipe 34 where the two meet to ensure a secure fitting of the fiber optic pipe 34 to the plug top 38. In one embodiment, the silicone based adhesive sealant should not extend past 8 millimeters above the plug top 38 surface.

FIG. 5 is a diagram illustrating a fully assembled fiber optic light pipe assembly 30. The remotely mounted LED emits light into the fiber optic pipe 34 which transmits the light to lens 32 which in turn casts the light onto the bobbin, effectuating illumination of the upper hemisphere of said bobbin.

In one embodiment, the LED would only turn on when flow is applied to the flow tube. This would be accomplished via a separate electronic mechanism. In one embodiment, this is accomplished through the use of separate electronic flow sensors, including a pressure transducer measuring the pressure rise through the resistance of the flow meter. In another embodiment, this mechanism can be accomplished via a switch on the flow control needle valve. This ensures that the illumination automatically turns on when flow is applied and automatically turns off when flow terminates, thereby helping to prevent flow systems from being inadvertently left on. This behavior has specific application to "auxiliary oxygen flow control" devices commonly used in anesthesia that, by design, are not decoupled from the oxygen supply when the anesthesia system is turned off.

Referring back to FIG. 1, the light enhanced flow tube 14 contains a bobbin 12 that is free to traverse the length of the flow tube 14. In one embodiment, the bobbin 12 is a substantially spherical white alumina ceramic ball. In one embodiment, the bobbin is ¼ inch in diameter. The white alumina ceramic has a more reflective quality than more traditional compositions, resulting in the light being spread over the entire upper hemisphere of the ball.

Figure 6:
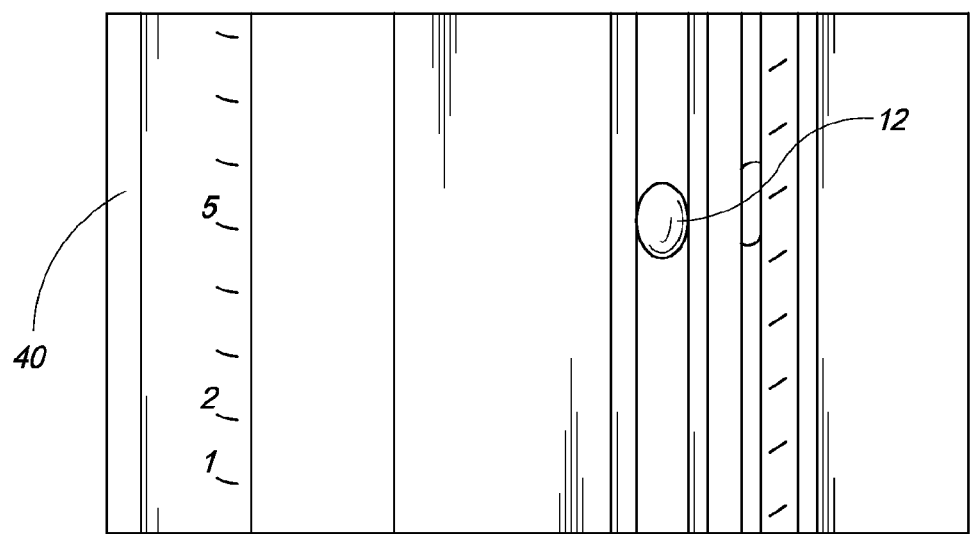
FIG. 6 is an illustration of a close-up view depicting the transition from light to dark of the illuminated bobbin adjacent to an electronic graphical flow display.

FIG. 6 is an illustration of a close-up view depicting the transition from light to dark of the illuminated bobbin 12 adjacent to an electronic graphical flow display 40. As shown in FIG. 6, the illumination of the entire upper hemisphere results in a light to dark line forming substantially at the middle of the bobbin 12, precisely where a user will take a visual flow reading. Therefore, when the LED transmits a light wave through the fiber optic pipe and out from the lens, it causes the upper portion of the bobbin to brighten which, relative to the lower portion of the bobbin, causes the creation of a solid light-based visual demarcation which can be used to accurately identify a level.

Figure 7:
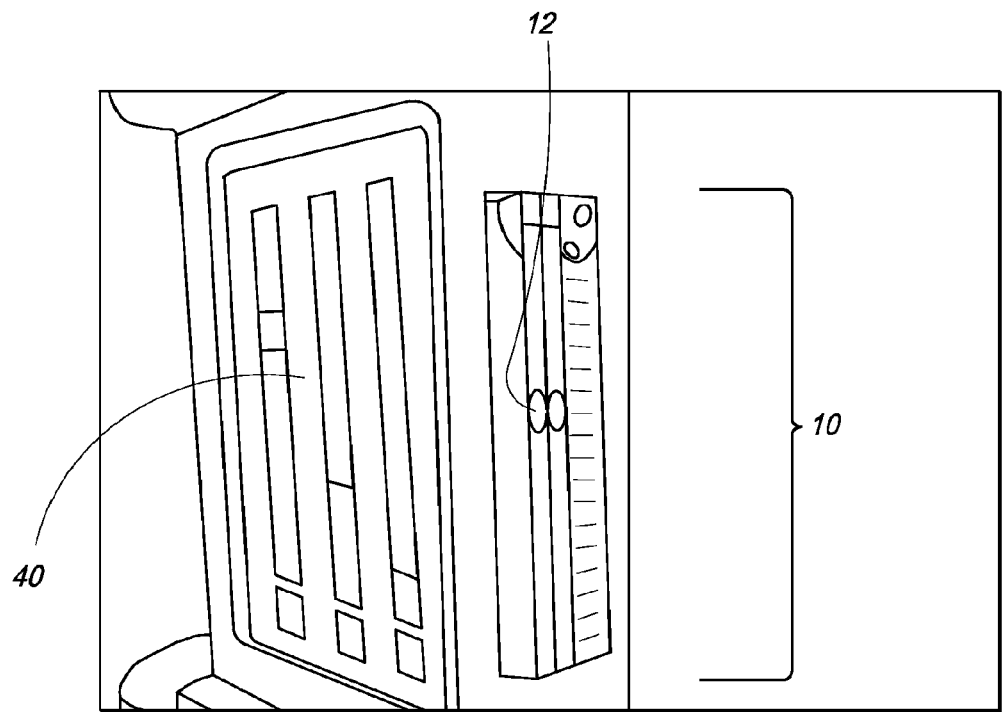
FIG. 7 is an illustration of one embodiment in which the light enhanced flow tube has been attached to an anesthesia machine adjacent to an electronic graphical flow display; and, FIG. 8 is an illustration of a straight on view of one embodiment in which the light enhanced flow tube has been attached to an anesthesia machine adjacent to an electronic graphical flow display.

FIG. 7 is a three dimensional diagram illustrating one embodiment in which the light enhanced flow tube 10 has been attached to an anesthesia machine adjacent to an electronic graphical flow display 40. In particular, it is advantageous to use flow tube designs in anesthesia applications as a back-up or an error checking device. The user will desire a mechanical device in the event of electronic failure and also as a means of coarsely spot checking readings against the graphical display. The angled face design of the acrylic block and the choice of a white alumina ceramic indicator ball as a bobbin enhance the effectiveness of the invention. Also, the use of the angled acrylic block surfaces allows for full visibility of the bobbin for the user but does not impinge on the front face geometry necessary for the best presentation of the graphical user interface.

Figure 8:
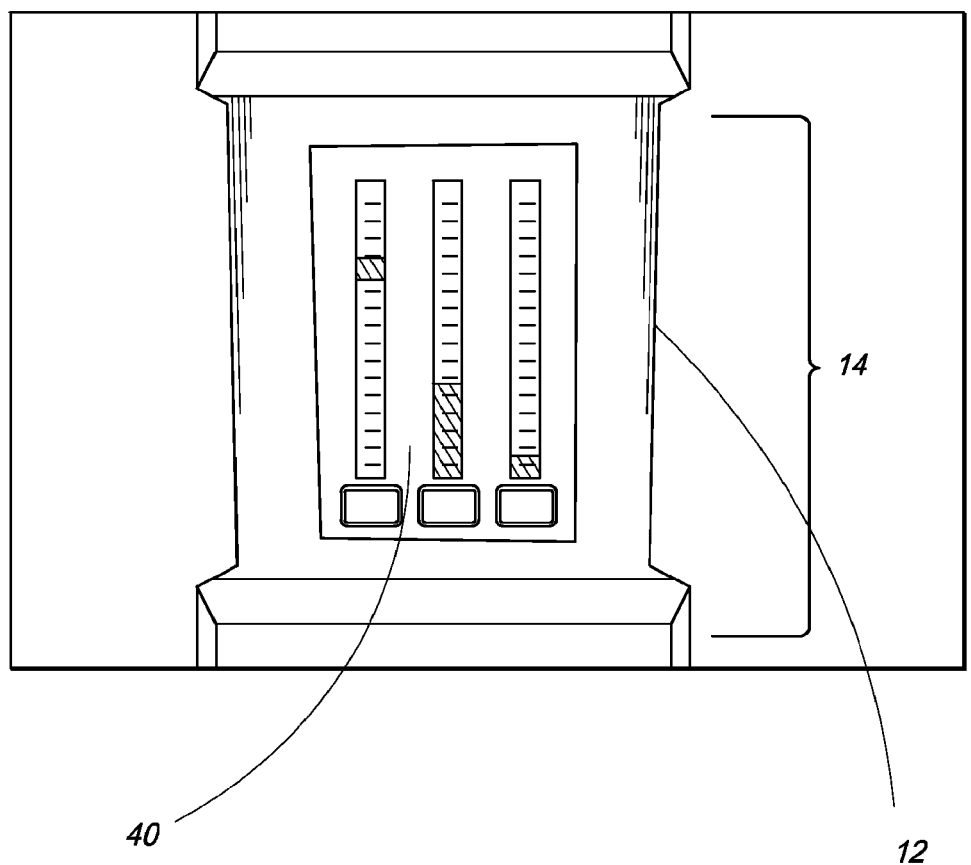

FIG. 8 is an illustration of a straight on view of one embodiment in which the light enhanced flow tube 14 has been attached to an anesthesia machine adjacent to an electronic graphical flow display 40. As shown in FIG. 8, in one embodiment, mounting the light enhanced flow tube 14 to the side of the electronic graphical flow display 40 allows the user to read both the electronic display and the mechanical bobbin simultaneously. In addition, the relatively small space occupied by the light enhanced acrylic block flow tube when viewed from the front allows the user to focus on the graphical display and use the mechanical reading as a back-up. The illuminated bobbin 12 seemingly matches the visuals provided by the graphical display 40, providing a convergence of old and new technologies.

In one embodiment, the light emitted by the LED is colored blue, in an effort to most closely match the visuals provided by the graphical display 40.

In another embodiment, the bobbin is a spherical stainless steel ball. When used as a bobbin, the stainless steel ball reflects the light from the LED as a single point.

In another embodiment, the light enhanced flow tube of the present invention can be used in any environment that is dark and/or dirty, thereby requiring an enhanced readability component. In addition, using the light enhanced flow tube in a dark and/or dirty environment would enable the user to assess the flow level at a glance.

In another embodiment, the light enhanced flow tube of the present invention can be used in any environment in which the flow tube needs to be read at some distance. The enhancement resulting from the illumination gives the user a sharper image of the relative readout with respect to the full height of the flow tube.

In another embodiment, the light enhanced flow tube of the present invention can be used in a household environment. The light enhanced flow tube can be used to enhance visualization of furnace flow levels, air conditioner flow levels, and radon remediation flow tubes (pull suction from under the house's foundation). In addition, these devices are often in darkened basements and so would benefit from the enhanced visualization afforded by the present invention in dark environments.

In another embodiment, the light enhanced flow tube of the present invention can be used in industrial environments. The light enhanced flow tube can be used in various types of fluid float applications using both liquids and gases. These environments can also be dark and/or dirty and the user would benefit from the light enhancement.

In another embodiment, the light enhanced flow tube of the present invention can be used in chemical applications. In another embodiment, the light enhanced flow tube of the present invention can be used in research applications. In another embodiment, the light enhanced flow tube of the present invention can be used in clean food processing applications.

Although certain illustrative embodiments and methods have been disclosed herein, it will be apparent from the foregoing disclosure to those skilled in the art that variations and modifications of such embodiments and methods may be made without departing from the spirit and scope of the invention. Accordingly, it is intended that the invention should be limited only to extent required by the appended claims and the rules and principals of applicable law.

The invention claimed is:

1. A method of operating a fluid flow gauging device to measure a flow of fluid, the method comprising:
    generating light from a source LED;
    transmitting said light through a fiber optic pipe, wherein said fiber optic pipe terminates in a lens;
    passing said light through said lens and into a top of a hollow tube, wherein said hollow tube has a length, a bottom and a bobbin and wherein the fluid flow gauging device comprises at least one unitary block of acrylic having a plurality of elongated sides parallel to the length of the hollow tube; and
    illuminating said bobbin, wherein the bobbin is adapted to traverse the length of the hollow tube based on an amount of fluid pressure applied.

2. The method of claim 1, wherein the source LED is positioned remote from the fluid flow gauging device.

3. The method of claim 1, further comprising positioning the fluid flow gauging device adjacent an electronic graphical flow display.

4. The method of claim 1, wherein the light is blue and said bobbin is a spherical stainless steel ball.

5. The method of claim 1, wherein the light is blue and said bobbin comprises white alumina ceramic.

6. The method of claim 1, wherein the light is white and said bobbin comprises white alumina ceramic.

7. The method of claim 1, further comprising automatically switching on the source LED when fluid flows.

8. The method of claim 1, comprising measuring a pressure rise of the fluid using a pressure transducer.

9. The method of claim 1, wherein one of said plurality of sides is a front face having a beveled portion.

10. The method of claim 9, wherein one of said plurality of sides is a side face having a beveled portion.

11. The method of claim 1 wherein the hollow tube further comprises an inlet port configured to receive pressurized gas into said hollow tube.

12. The method of claim 11 wherein the hollow tube further comprises an outlet port configured to enable an exit of said pressurized gas from said hollow tube.

* * * * *